(12) United States Patent
Ainger et al.

(10) Patent No.: US 7,183,243 B2
(45) Date of Patent: Feb. 27, 2007

(54) COMPOSITIONS FOR WASHING AND CONDITIONING HAIR

(75) Inventors: Nicholas John Ainger, Wirral (GB); Anand Ramchandra Mahadeshwar, Wirral (GB); Neil Scott Shaw, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 105 days.

(21) Appl. No.: 10/534,630

(22) PCT Filed: Oct. 30, 2003

(86) PCT No.: PCT/EP03/12066

§ 371 (c)(1), (2), (4) Date: May 11, 2005

(87) PCT Pub. No.: WO2004/043414

PCT Pub. Date: May 27, 2004

(65) Prior Publication Data

US 2006/0058205 A1    Mar. 16, 2006

(30) Foreign Application Priority Data

Nov. 12, 2002 (GB) .................. 0226380.4
Oct. 6, 2003 (GB) .................. 0323276.6

(51) Int. Cl.
*C11D 3/37* (2006.01)
*C11D 9/36* (2006.01)

(52) U.S. Cl. ............... 510/121; 510/119; 510/122; 510/466; 424/70.1; 424/70.11; 424/70.12; 424/70.21; 424/70.22; 424/70.31

(58) Field of Classification Search ............... 424/70.1, 424/70.11, 70.12, 70.21, 70.22, 70.31; 510/119, 510/121, 122, 466
See application file for complete search history.

(56) References Cited

U.S. PATENT DOCUMENTS

| | | | |
|---|---|---|---|
| 3,958,581 A | 5/1976 | Abegg et al. | |
| 4,009,256 A | 2/1977 | Nowak, Jr. et al. | |
| 5,747,436 A * | 5/1998 | Patel et al. ................ | 510/124 |
| 5,759,527 A * | 6/1998 | Patel et al. ............. | 424/70.11 |
| 5,874,073 A * | 2/1999 | Kaiser et al. ............ | 424/70.11 |
| 5,977,036 A * | 11/1999 | Guskey ..................... | 510/121 |
| 6,010,690 A * | 1/2000 | Varco ...................... | 424/70.13 |
| 6,090,773 A * | 7/2000 | Lukenbach et al. ......... | 510/475 |
| 6,444,628 B2 | 9/2002 | Nocerino et al. | |
| 6,495,498 B2 * | 12/2002 | Niemiec et al. ............ | 510/122 |
| 6,927,196 B2 * | 8/2005 | Snyder et al. .............. | 510/124 |
| 2003/0108501 A1* | 6/2003 | Hofrichter et al. ........ | 424/70.1 |
| 2004/0146475 A1* | 7/2004 | Peffly et al. ............. | 424/70.13 |

FOREIGN PATENT DOCUMENTS

| | | |
|---|---|---|
| EP | 0 455 185 A2 | 11/1991 |
| WO | 95/22311 | 8/1995 |
| WO | 96/31188 | 10/1996 |

* cited by examiner

*Primary Examiner*—Charles Boyer
(74) *Attorney, Agent, or Firm*—Karen E. Klumas

(57) ABSTRACT

Hair washing compositions are disclosed which comprise cleansing surfactant, water, first and second cationic polymers having at pH7 a charge density from 0.2 to 1 meq/gm and from 1.3 to 3 meq/gm respectively, and droplets of a water-insoluble conditioning oil of diameter 4 micrometres or less. The compositions provide cleansing with conditioning and low friction and ease of combing for wet and dry hair.

14 Claims, No Drawings

COMPOSITIONS FOR WASHING AND CONDITIONING HAIR

TECHNICAL FIELD

The invention is concerned with rinse-off hair-conditioning compositions which are applied to the hair or body and then substantially rinsed away. It is particularly concerned with hair shampoo compositions and shower gels, which both clean the hair and provide conditioning benefit to the hair. More specifically, it is concerned with hair-washing compositions which have the effect of providing low friction and ease of combing to the hair when dry.

BACKGROUND AND PRIOR ART

Compositions which provide a combination of cleansing and conditioning to the hair are know in the art. Such shampoo or shower-gel compositions typically comprise one or more surfactants for shampooing or cleansing purposes and one or more conditioning agents. Typically, these conditioning agents are water-insoluble oily materials, cationic polymers or cationic surfactants. One purpose of the conditioning agent is to make the hair easier to comb when wet and more manageable when dry, e.g. less static and fly-away. Another important role, especially for water-insoluble oily conditioning agents, is to provide low friction and ease of combing for dry hair.

It is known to incorporate cationic polymers in hair-washing compositions. For instance. U.S. Pat. No. 6,444,628 discloses an aqueous shampoo comprising, in addition to water, an anionic cleansing surfactant, a cationic polymer and a monoalkyl quaternary ammonium compound.

Such cationic polymers are often used in combination with water-insoluble conditioning oils in order to improve the deposition of the conditioning oils onto the hair. U.S. Pat. No. 3,753,916 discloses the use of cationic polymers as deposition aids.

It has now been found that by using a specific combination of cationic polymers in a hair-washing compositions which comprise small droplets of a water-insoluble oily conditioning agent, problems encountered with prior art washing and conditioning compositions can be overcome. In particular, improved low friction and ease of combing can be obtained for the hair after drying, with a reduction in the heavy, greasy feel that many consumers experience when high charge density cationic polymers and oily conditioning agents are combined in shampoos.

SUMMARY OF INVENTION

In a first aspect, the invention provides a hair-washing composition comprising
   a) from 1 to 50% by weight of a cleansing surfactant,
   b) from 0.01 to 0.5% by weight of a first cationic polymer having a mean charge density at pH7 from 0.2 to 1.0 meq per gram,
   c) from 0.01 to 0.4% by weight of a second cationic polymer having a mean charge density at pH7 from 1.3 to 3.0 meq per gram,
   d) more than 40% by weight of water, and
   e) from 0.1 to 10% by weight of discrete, dispersed droplets of a water-insoluble conditioning oil with a mean diameter ($D_{3,2}$) of 4 micrometres or less, characterised in that both the first cationic polymer and the second cationic polymer consist essentially of the same monomeric units.

DETAILED DESCRIPTION OF THE INVENTION

By water-insoluble, it is meant that the material so described has a solubility in water at 25° C. of 0.1% by weight or less.

All viscosities mentioned are kinematic viscosities unless otherwise specified, and are to be measured at 25° C. using calibrated capillary glass viscometers under gravity flow conditions.

All molecular weights referred to are weight average ($M_w$) molecular weights unless otherwise specified. The compositions provided by the invention are aqueous compositions, used by massaging them into the hair followed by rinsing with clean water prior to drying the hair.

Optionally, a separate conditioning formulation may be applied after rinsing and before drying, but this may not be necessary as the compositions of the invention are intended to provide both cleansing and conditioning to the hair.

The compositions provided by the invention comprise more than 40% by weight of water, preferably more than 50%, more preferably more than 65%.

Cleansing Surfactant

Hair-washing compositions according to the invention comprise one or more cleansing surfactants from the group which is cosmetically acceptable and suitable for topical application to the hair.

Suitable cleansing surfactants, which may be used singularly or in combination, are selected from anionic, nonionic, amphoteric and zwitterionic surfactants, and mixtures thereof.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n is from 1 to 3), ammonium lauryl sulphate and ammonium lauryl ether sulphate(n)EO, (where n is from 1 to 3).

Mixtures of any of the foregoing anionic cleansing surfactants may also be suitable.

The total amount of anionic cleansing surfactant in shampoo compositions of the invention is generally from generally from 0.5 to 45, preferably from 1.5 to 35, more preferably from 5 to 20 percent by weight of the composition.

Co-Surfactant

The composition can include co-surfactants, to help impart aesthetic, physical or cleansing properties to the composition.

A preferred example is an amphoteric or zwitterionic surfactant, which can be included in an amount ranging from 0 to about 8, preferably from 1 to 4 percent by weight of the composition.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

The composition according to the invention can also optionally include one or more cationic co-surfactants included in an amount ranging from 0.01 to 10, more preferably from 0.05 to 5, most preferably from 0.05 to 2 percent by weight of the composition.

The total amount of cleansing surfactant (including any co-surfactant, and/or any emulsifier) in compositions of the invention is generally from 1 to 50, preferably from 2 to 40, more preferably from 10 to 25 percent by weight of composition.

A preferred blend of cleansing surfactants is a combination of ammonium lauryl ether sulphate, ammonium lauryl sulphate, PEG 5 cocamide and cocamide MEA (CTFA designations).

Cationic Polymer

Compositions according to the invention comprise from 0.01 to 0.5% by weight of a first cationic polymer having a mean charge density at pH7 from 0.2 to 1.0 meq per gram, and from 0.01 to 0.4% by weight of a second cationic polymer having a mean charge density at pH7 from 1.3 to 3.0 meq per gram.

It is essential for the invention that both the first and second cationic polymer consist essentially of the same monomers and cationic substituents, by which it is meant that the polymers comprise 95% or more by weight of the same monomers. When the polymers are cationically substituted homopolymers or copolymers, then the cationic substituent must be essentially the same for each polymer, but the degree of substitution will be different for the first and the second homopolymer in order to give the required charge densities for the two cationic polymers.

The cationic polymers may be homopolymers which are cationically substituted or may be formed from two or more types of monomers. The molecular weight of each polymer will generally be between 100 000 and 2 000 000 Dalton. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range for each of the first and second cationic polymers.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives.

Cationic polysaccharide polymers suitable for use in compositions of the invention include momomers of the formula:

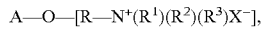

$$A—O—[R—N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

The first cationic polymer will generally be present in compositions of the invention at levels of from 0.01 to 0.5, preferably from 0.05 to 0.4, more preferably from 0.1 to 0.3 percent by weight of the composition.

The second cationic polymer will generally be present in compositions of the invention at levels of from 0.01 to 0.4, preferably from 0.05 to 0.35, more preferably from 0.1 to 0.3 percent by weight of the composition.

The cationic charge density of the polymer is suitably determined via the Kjeldahl method as described in the US Pharmacopoeia under chemical tests for nitrogen determination.

It is preferred if the first and cationic polymers are both cationically substituted guar gums, both cationically substituted hydroxyethylcelluloses or both cationic polyacrylamides, because of the relative ease of manufacture and wide availability of these polymers.

It is particularly preferred if both the first and second cationic polymers are guar hydroxypropyltrimethylammonium chlorides.

The first cationic polymer has a mean charge density from 0.2 to 1.0 meq/gm, preferably from 0.3 to 0.9 meq/gm.

The second cationic polymer has a mean charge density from 1.3 to 3 meq/gm, preferably from 1.4 to 2.5, more preferably from 1.5 to 1.8.

If the charge density of the second cationic polymer is higher than the specified range, it is found that the hair may feel heavy or greasy. This is thought to be due to excessive deposition of the second polymer. If the charge density of the first polymer is lower than the specified range, it is found that the wet conditioning of the composition may be inadequate.

Water-Insoluble Conditioning Oil

Compositions according to the invention comprise from 0.1 to 10% by weight of a water-insoluble conditioning oil. This may be a non-silicone hydrophobic oil but is more preferably a silicone conditioning agent. Preferably the conditioning agent is non-volatile, meaning that it has a vapour pressure of less than 1000 Pa at 25° C. The conditioning oil is present in the composition as discrete emulsion droplets.

The total amount of water-insoluble conditioning oil in compositions of the invention is preferably from 0.2% to 5%, more preferably from 0.5% to 3% by weight of the total composition.

Emulsified hydrophobic conditioning oils for use in the shampoo or shower gel compositions of the invention suitably have Sauter mean droplet diameter ($D_{3,2}$) in the composition of 4 micrometres or less, preferably 2 micrometres or less, more preferably 1 micrometer or less.

A suitable method for measuring the Sauter $D_{3,2}$ mean diameter is by laser light scattering using an instrument such as a Malvern Mastersizer.

Silicone Conditioning Oil

It is preferred if the water-insoluble conditioning oil of compositions of the invention is emulsified droplets comprising, preferably consisting essentially of, a silicone conditioning oil.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the silicone itself (not the emulsion or the final hair conditioning composition) is typically from 350 to 200,000,000 mm$^2$sec$^{-1}$ at 25° C. Preferably the viscosity is at least 5,000 mm$^2$sec$^{-1}$ at 25° C., more preferably at least 10,000 mm$^2$sec$^{-1}$. Preferably the viscosity does not exceed 20,000,000 mm$^2$sec$^{-1}$, more preferably 10,000,000 mm$^2$sec$^{-1}$, most preferably 5,000,000 mm$^2$sec$^{-1}$.

Viscosities are generally provided by suppliers of silicones, either as measured or as deduced from their molecular weight.

It is preferred if the silicone oil also comprises a functionalised silicone. Suitable functionalised silicones include, amino-, carboxy-, betaine-, quaternary ammonium-, carbohydrate-, hydroxy- and alkoxy-substituted silicones. Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the definition of the present invention. However, a polydimethylsiloxane having hydroxyl substitutions along the polymer chain is considered a functionalised silicone.

A preferred class of functionalised silicone for inclusion in compositions of the invention is amino functional silicone. By "amino functional silicone" is meant a silicone containing at least one primary, secondary or tertiary amine group, or a quaternary ammonium group. Examples of suitable amino functional silicones include: polysiloxanes having the CTFA designation "amodimethicone", Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones). Suitable quaternary silicone polymers are described in EP-A-0 530 974. A preferred quaternary silicone polymer is K3474, ex Goldschmidt.

Another preferred functional silicone for use as a component in the hydrophobic conditioning oil is an alkoxy-substituted silicone. Such molecules are known as silicone copolyols and have one or more polyethyleneoxide or polypropyleneoxide groups bonded to the silicone polymer backbone, optionally through an alkyl linking group.

An example of a type of silicone copolyol useful in compositions of the invention has a molecular structure according to the formula depicted below:

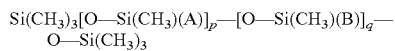

In this formula, A is an alkylene chain with from 1 to 22 carbon atoms, preferably 4 to 18, more preferably 10 to 16. B is a group with the structure: —(R)—(EO)$_r$(PO)$_s$—OH wherein R is a linking group, preferably an alkylene group with 1 to 3 carbon atoms. Preferably R is —(CH$_2$)$_2$—. The mean values of r and s are 5 or more, preferably 10 or more, more preferably 15 or more. It is preferred if the mean values of r and s are 100 or less. In the formula, the value of p is suitably 10 or more, preferably 20 or more, more preferably 50 or more and most preferably 100 or more. The value of q is suitably from 1 to 20 wherein the ratio p/q is preferably 10 or more, more preferably 20 or more. The value of p+q is a number from 11 to 500, preferably from 50 to 300.

Suitable silicone copolyols have an HLB of 10 or less, preferably 7 or less, more preferably 4 or less. A suitable silicone copolyol material is DC5200, known as Lauryl PEG/PPG—18/18 methicone (INCI name), available from Dow Corning.

Hydrophile/Lipophile balance or HLB is a well known parameter used by those skilled in the art to characterise surface active molecules and emulsifiers. Suitable methods for the experimental determination of HLB are in Griffin W. C, Journal of the Society of Cosmetic Chemists, volume 1 page 311 (1949). The commercially available silicone copolyols are supplied along with a value of their HLB by Dow Corning.

It is preferred to use a combination of amino and non-functional silicones. In particular, when the water-insoluble oil is a silicone oil blend, it is preferred if the silicone oil blend comprises
(i) from 50 to 95% by weight of the total weight of silicone oil of a polydimethylsiloxane gum having a molecular weight of 200,000 unified mass units or more and
(ii) from 5 to 50% by weight of the total weight of silicone oil a second silicone which is an amino-functionalised polydimethylsiloxane having a molecular weight of less than 200,000 unified mass units.

Suitable amino-functionalised silicones for such a blend are described in EP 455,185 (Helene Curtis) and include trimethylsilylamodimethicone as depicted below, and are sufficiently water-insoluble so as to be useful in compositions of the invention:

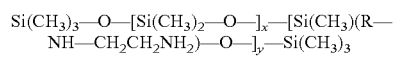

wherein x+y is a number from about 50 to about 500, and the mole percent amine functionality is from 0.3% to 8%, and wherein R is an alkylene group having from 2 to 5 carbon atoms. Preferably, the number x+y is from 100 to 300, and the mole percent amine functionality is from 0.3% to 8%.

As expressed here, the weight percent amine functionality is measured by titrating a sample of the amino-functionalised silicone against alcoholic hydrochloric acid to the bromocresol green end point. The mole percent amine is calculated using a molecular weight of 45 (corresponding to CH$_3$—CH$_2$—NH$_2$).

Suitably, the mole percent amine functionality measured and calculated in this way is from 0.3% to 8%, preferably from 0.5% to 4%.

An example of a commercially available amino-functionalised silicone useful in the silicone component of the composition of the invention is DC-8220 available from Dow Corning, which has a viscosity of 150 mm$^2$s$^{-1}$ at 25° C. and a mole percent amine functionality of 2.0%.

Polydimethylsiloxane silicone gums are also a component of the preferred silicone oil blend described above.

The polydimethylsiloxane gum is present at a level of at least 50 wt %, preferably at least 60 wt % based on the total weight of the silicone component.

The polydimethylsiloxane gum suitably has a viscosity of at least 500,000 mm2/sec, preferably at least 600,000 mm2/sec, more preferably at least 1,000,000 mm2/sec at 25° C.

Suitably, the first silicone has a molecular weight of at least 200,000 Dalton preferably at least 400,000 Dalton, more preferably at least 500,000 Dalton.

Suitable silicone gums include SE30, SE54 and SE76 (ex General Electric Silicones).

The silicones may be added to the composition as a fluid and subsequently emulsified, but preferably are added as pre-formed emulsions for ease of processing. Preferably, the pre-formed silicone emulsions additionally comprise a suitable emulsifier such as dodecylbenzenesulphonic acid, or are emulsified using the surface active block copolymer as the emulsifier. A preferred form of silicone oil emulsion is one which has been preferred by mechanical emulsification using a high shear mixer.

Non-Silicone Conditioning Oil

Compositions according to the present invention may comprise a dispersed, non-volatile, water-insoluble oily non-silicone conditioning agent as the water-insoluble conditioning oil.

Suitable oily or fatty materials are selected from hydrocarbon oils, fatty esters and mixtures thereof.

Straight chain hydrocarbon oils will preferably contain from about 12 to about 30 carbon atoms. Also suitable are polymeric hydrocarbons of alkenyl monomers, such as C2–C6 alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Another suitable material is polyisobutylene.

Suitable fatty esters are characterised by having at least 10 carbon atoms, and include esters with hydrocarbyl chains derived from fatty acids or alcohols, Monocarboxylic acid esters include esters of alcohols and/or acids of the formula R' COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as C1–C22 carboxylic acids. Preferred materials include cocoa butter, palm stearin, sunflower oil, soyabean oil and coconut oil.

Preferably, the viscosity of the non-silicone conditioning oil itself is from 350 to 10,000,000 $mm^2sec^{-1}$ at 25° C. More preferably the viscosity is at least 5,000 $mm^2sec^{-1}$ at 25° C., most preferably at least 10,000 $mm^2sec^{-1}$. Preferably the viscosity does not exceed 500,000 $mm^2sec^{-1}$.

Other Ingredients

Compositions according to the invention may contain other ingredients suitable for use in hair cleansing and conditioning compositions. Such ingredients include but are not limited to: fragrance, suspending agents, amino acids and protein derivatives, viscosity modifiers and preservatives.

The invention will now be further illustrated by reference to the following, non-limiting examples.

EXAMPLES

Compositions were prepared according to the formulations detailed in tables 1 and 2. All ingredients are expressed in the tables by weight percent of the total formulation, and as level of active ingredient.

TABLE 1

| Ingredient | Weight Percent Active |
| --- | --- |
| Anionic Surfactant | 10 |
| Amphoteric Surfactant (CAPB) | 3 |
| Cationic Guar (See table 2) | 0.2 |
| Emulsified silicone | 1.5 |
| Minors and Water | to 100 |

The anionic surfactant is an Ether Sulphate (1EO), CAPB is coco amidopropyl betaine. The cationic guar is either Jaguar C17 or Jaguar C13S or a combination of the two as detailed below in table 2. The emulsified silicone is droplets of a aminosilicone (mol wt 32,000 and mole % amine content of about 1.75%) and polydimethylsiloxane gum (mol wt 700,000 u) with a mean $D_{3,2}$ droplet diameter of 1 micron.

TABLE 2

| Example | JaguarC13S | JaguarC17 | Friction | Deposition |
| --- | --- | --- | --- | --- |
| A | 0.2 | 0 | 25643 | 108 |
| 1 | 0.175 | 0.025 | 22827 | 301 |
| 2 | 0.15 | 0.05 | 18896 | 515 |
| 3 | 0.125 | 0.075 | 16284 | 583 |
| 4 | 0.1 | 0.1 | 18098 | 615 |
| B | 0 | 0.2 | 15576 | 659 |

0.25g/5 cm switches of hair which had been cleaned with a solution of 14% SLES 2EO and 2% cocoamidopropyl betaine in water followed by extensive rinsing, were used as the basis for the following analysis. The test shampoo was diluted to 1 in 10 by weight with distilled water and stirred throughout with a magnetic stirrer. 5 switches were placed in one half of a petri dish. 1.5 mls of diluted shampoo was placed along the length of the switches which were then agitated in the dish for 30 seconds, followed by a rinse for 30 seconds under tap water (12° French hard) at 40° C., with a flow rate set at 3–4 liters per minute. The washing process using the test shampoo solution was repeated followed again by rinsing. The switches were then allowed to dry naturally at 25° C. and a relative humidity of 45 to 60%.

The amount of silicone deposited on the hair samples was measured using X-ray fluorescence spectrometry (measured in parts per million (ppm) of elemental silicon.

The friction was measured using a laboratory technique with a commercially available texture analyser TA XT2i ex Stable Microsystems.

Compositions according to Examples B and 3 were each compared in a home-use test against a benchmark formulation with only 0.2% Jaquar C13S corresponding to formula A. Each formulation was scored by the users for a set of performance attributes.

Both the examples B and 3 were significantly preferred over the benchmark in the home-use test for the attribute "smooth feel" of the hair (90% and 95% significance respectively). However, Example B gave a significantly (90%) poorer score than the benchmark for "Greasy Scalp". By contrast, example 3 was preferred over the benchmark (directionally but not significantly) on greasy scalp.

The home-use test results, and the friction and deposition test results, demonstrate that compositions according to the invention are able to achieve conditioning performance equivalent to compositions with a high charge density cationic polymer alone, yet without the negative of greasy scalp feel.

The invention claimed is:

1. A hair-washing composition comprising
   a) from 1 to 50% by weight of a cleansing surfactant,
   b) from 0.01 to 0.5% by weight of a first cationic polymer having a mean charge density at pH7 from 0.2 to 1.0 meq per gram,
   c) from 0.01 to 0.4% by weight of a second cationic polymer having a mean charge density at pH7 from 1.3 to 3.0 meq per gram,
   d) more than 40% by weight of water, and
   e) from 0.1 to 10% by weight of discrete, dispersed droplets of a water-insoluble conditioning oil with a mean diameter ($D_{3,2}$) of 4 micrometres or less, characterised in that both the first cationic polymer and the second cationic polymer consist essentially of the same monomeric units and cationic substituents.

2. A composition according to claim 1 wherein the first and second cationic polymers are both cationically substituted guar gums.

3. A composition according to claim 2 wherein the first and second cationic polymers are both guar hydroxypropyltrimethylammonium chlorides.

4. A composition according to claim 1 wherein the first and second cationic polymers are both cationically substituted hydroxyethyl celluloses.

5. A composition according to claim 1 wherein the first and second cationic polymers are both cationic polyacrylamides.

6. A composition according to claim 1 wherein the cleansing surfactant is selected from the group consisting of anionic surfactants, amphoteric surfactants, zwitterionic surfactants, nonionic surfactants and mixtures thereof.

7. A composition according to claim 1 wherein the water-insoluble conditioning oil comprises a silicone oil.

8. A composition according to claim 7 wherein the silicone oil comprises
    (i) from 50 to 95% by weight of the total weight of silicone oil of a polydimethylsiloxane gum having a molecular weight of 200,000 unified mass units or more and
    (ii) from 5 to 50% by weight of the total weight of silicone oil of a second silicone which is an amino-functionalised polydimethylsiloxane having a molecular weight of less than 200,000 unified mass units.

9. A composition according to claim 8, in which the polydimethylsiloxane gum has a viscosity of 500,000 $mm^2$/sec or more at 25° C.

10. A composition according to claim 8, in which the amino-functional polydimethylsiloxane has a viscosity of less than 500,000 $mm^2$/sec at 25° C.

11. A composition according to claim 8, in which the amino-functionalised silicone has a mole percent amino functionality from 0.3 to 8.

12. A composition according to claim 8, in which the weight ratio of the polydimethylsiloxane gum to the amino-functional polydimethylsiloxane is from 15:1 to 1:1.

13. A composition according to claim 1, in which the water-insoluble conditioning oil is in the form of a mechanically generated emulsion.

14. A method of washing and conditioning hair by massaging a composition according to claim 1 into the hair followed by rinsing prior to drying the hair.

* * * * *